United States Patent [19]

Dagger et al.

[11] Patent Number: 4,843,163

[45] Date of Patent: Jun. 27, 1989

[54] CERTAIN 3-(2-PHENETHYL)-1-CARBAMOYLOX- YPYRIDINIUM HALIDE INTERMEDIATES

[75] Inventors: Raymond E. Dagger, Warminster; Linda A. Motyka, Exton, both of Pa.

[73] Assignee: SmithKline Beckman Corporation, Philadelphia, Pa.

[21] Appl. No.: 127,840

[22] Filed: Dec. 2, 1987

[51] Int. Cl.$^4$ .................. C07D 213/18; C07D 401/12
[52] U.S. Cl. ..................................... 546/194; 546/281; 546/286; 546/347
[58] Field of Search ........................ 546/194, 281, 347

[56] References Cited

U.S. PATENT DOCUMENTS 3,326,924  6/1967  Villani ..................................... 546/93
3,357,986  12/1967  Villani ..................................... 546/93

*Primary Examiner*—Alan L. Rotman
*Attorney, Agent, or Firm*—Stuart R. Suter; Alan D. Lourie

[57] ABSTRACT

3-(2-Phenethyl)-1-carbamoyloxypyridinium halide is an intermediate for the preparation of the antihistamine azatadine.

5 Claims, No Drawings

CERTAIN 3-(2-PHENETHYL)-1-CARBAMOYLOX-YPYRIDINIUM HALIDE INTERMEDIATES

This invention relates to intermediates for the preparation of azatadine and to a process for preparing and using those intermediates.

BACKGROUND OF THE INVENTION

Aza-dibenzocycloheptenes are described in U.S. Pat. No. 3,326,924 as having antihistaminic, antiserotonin and antianaphylactic activity and as useful in the treatment of allergic disorders such as urticaria, seasonal rhinitis and pollen sensitivity. One of these compounds is azatadine which is represented by the following formula:

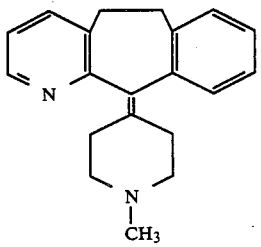

This compound is an antihistamine used in treatment of colds.

According to U.S. Pat. No. 3,326,924, the benzenoid portion of the aza-dibenzocycloheptene nucleus may be substituted by substituents such as lower alkyl, halogen, trifluoromethyl, hydroxy and lower alkoxy. The intermediates and process of the present invention are useful in preparing azatadine as well as the substituted compounds.

In a process described in U.S. Pat. No. 3,326,924, 3-(2-phenethyl)-2-cyanopyridine is prepared by reacting 3-(2-phenethyl)pyridine-1-oxide with dimethylsulfate and then with aqueous sodium cyanide. A process to convert the cyanopyridine to an aza-dibenzocycloheptene by cyclizing to give the 5-keto-aza-dibenzocycloheptene, then reacting with a Grignard reagent, e.g., 1-methyl-4-piperidinyl magnesium chloride, to give a 5-(1-methyl-4-piperidinyl)aza-dibenzocycloheptene-5-ol, which is dehydrated to give the exocyclic 5-(1-methyl-piperidylidenyl) compound, e.g., azatadine, is also described in U.S. Pat. No. 3,326,924.

It has been reported by Fife et al., *Heterocycles* 22:1121-4(1984) that 3-methyl-1-methoxypyridinium methylsulfate reacted with cyanide ion to give 3-methyl-2-cyanopyridine and "high percentages" of the 4-cyanopyridine isomer. In Table 1 on page 1122, Fife et al. reported that the 4-cyano compound was gobtained in 69% yield and 3-methyl-2-cyanopyridine was obtained in 24% yield.

Also, Fife et al., cited hereabove and *Heterocycles* 22:93-96(1984), reported the reaction of 3-methylpyridine-1-oxide with dimethyl-carbamoyl chloride to give 3-methyl-1-dimethylcarbamoyloxypyridinium chloride. Reaction of this pyridinium salt with potassium cyanide in water gave 3-methyl-2-cyanopyridine (89%) and the 6-isomer (11%).

A review entitled "Cyanation in the Pyridine Series: Synthetic Applications of the Reissert-Henze and Related Reactions" by Fife et al., *Heterocycles* 22:2375-2394(1984) includes the cyanation of 3-methylpyridine-1-oxide using dimethylcarbamoyl chloride.

None of these references disclose a 3-(2-phenethyl)-1-carbamoyloxypyridinium halide intermediate.

The Invention

The intermediates of the present invention are represented by the following Formula I:

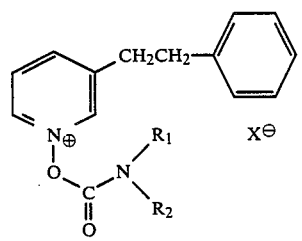

Formula I in which:

$R^1$ and $R_2$ are $C_{1-4}$ alkyl or, taken together with the nitrogen atom to which they are attached, pyrolidinyl or piperidinyl; and X is chloro, bromo or iodo.

Preferably, $R_1$ and $R_2$ are methyl or ethyl, most preferably, methyl.

X is preferably chloro.

These intermediates are useful in preparing azatadine. Also, an object of this invention is the process by which 1) the carbamoyloxy intermediates are prepared from the pyridine-N-oxide and the carbamoyl halide and 2) the carbamoyloxy intermediates are converted to the 2-cyanopyridine compound. The process of this invention using the intermediates of Formula I provides advantages over the dimethylsulfate process of U.S. Pat. No. 3,326,924, that is, it provides an improved product isomer distribution, easier product purification and improved yield.

The process of this invention is represented as follows:

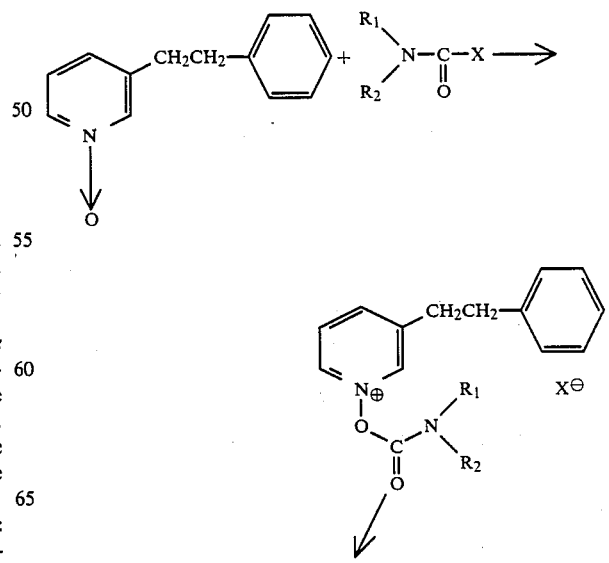

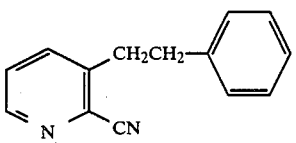

The terms $R_1$, $R_2$ and X are as defined above.

According to the first step in the above process, 3-(2-phenethyl)-pyridine-1-oxide is reacted with a substituted carbamoyl halide. This step may be carried out in the presence of an additional solvent such as toluene, ethyl acetate, methylene chloride or chloroform. The temperature at which the reaction is carried out ranges from ambient to 80° C. The carbamoyloxy salt intermediate may precipitate from the reaction mixture. The carbamoyloxy intermediate may (or may not) be isolated, purified and characterized before the second step of the process is carried out.

According to the second step of the process the carbamoyloxy intermediate is treated with an alkali metal cyanide in aqueous solution. The reaction is carried out at 7°-28° C. After work-up, the 3-(2-phenethyl)-2-cyanopyridine is obtained with small amounts of the corresponding 6-cyano compound and substantially none of the 4-cyano isomer.

3-(2-Phenethyl)pyridine-1-oxide is known to the art and the carbamoyl halides are also known to the art or may be prepared by known methods.

The following examples are intended to illustrate the invention but are not limiting. All temperatures are in degrees Centigrade.

EXAMPLE 1

A solution of 380 g (1.85 mole) of 3-(2-phenethyl)-pyridine-1-oxide in 1.0 l of ethyl acetate is heated, while stirring, to reflux. Dimethylcarbamoyl chloride [220 ml (253.8 g @ 97%), 2.31 mole] is added quickly to the refluxing solution and the resultant mixture is heated to reflux for 15 minutes, then cooled rapidly to 20°-25°. While cooling, 2 l of deionized water is added to the cooled reaction mixture. The resultant mixture is agitated vigorously for 10-15 minutes while cooling the mixture to 25°-30°.

The mixture is transferred to a separatory funnel. The bottom aqueous layer contains 3-(2-phenethyl)-1-dimethyl-carbamoylpyridinium chloride. The aqueous solution is separated from the organic layer and added slowly to a cold stirred solution of 177 g (2.72 mole) of potassium cyanide in 2.6 l of deionized water, the addition rate being controlled so that the reaction temperature does not exceed 20°. After the addition is complete, the mixture is stirred for 2 hours while cooling and maintaining the temperature at 5°-10°.

The reaction may be followed by gas chromatography. When the reaction is over, the mixture is warmed to 20°-25°. Ethyl acetate (2.4 l) is added and the mixture is agitated vigorously for 10 minutes, then transferred to a separatory funnel. The bottom (aqueous) layer is treated with 2.4 l of ethyl acetate, agitated vigorously and transferred to a separatory funnel. The combined top organic layers are washed with deionized water (1.8 l), then with twice with 10% aqueous hydrochloric acid (1.8 l). The organic solution is dried over 125 g of potassium carbonate, filtered, concentrated and distilled to give 3-(2-phenethyl)-2-cyanopyridine, b.p. 160°-165°/0-.4-0.5 mm Hg.

This procedure produced, after distillation, 58% yield of the product, 5-(2-phenethyl)-2-cyanopyridine, as a 13:1 mixture with the 6-cyano isomer.

EXAMPLE 2

A mixture of .10 g (50.2 mmole) of 3-(2-phenethyl)-pyridine-1-oxide and 20 ml of toluene is stirred and heated to 75°. Dimethylcarbamoyl chloride (11.68 g, 106.4 mmole) is added in one portion. The reaction is exothermic to 87° as a white oil precipitates. Within 12 minutes the reaction mixture is cooled to 75° and stirred for 2 hours at 70°-75°, then transferred to a separatory funnel to isolate 3-(2-phenethyl)-1-dimethylcarbamoyl-pyridinium chloride as an oily bottom layer upon settling.

To the pyridinium salt is added 50 ml of water. The mixture is shaken to take the salt into water. The water extract is added over 5 minutes to a cold (15°) stirred solution of potassium cyanide (4.88 g, 75 mmole) in 40 ml of water. The reaction mixture is exothermic to 37°. The mixture is stirred for 2 hours in an ice water bath. The mixture is extracted with toluene, dried over potassium carbonate, filtered, concentrated and dissolved in 50 ml of ethyl acetate. The ethyl acetate solution is extracted twice with 25 ml of 10% HCl. The extracts are combined, neutralized with sodium bicarbonate and extracted twice with methylene chloride. The extracts are combined, dried over potassium carbonate, filtered and concentrated to give 2-cyano isomer, 3-(2-phenethyl)-2-cyanopyridine, and the 6-cyano isomer, 3-(2-phenethyl)-6-cyanopyridine, in a ratio of 8.7:1.

What is claimed is:

1. A compound of the formula:

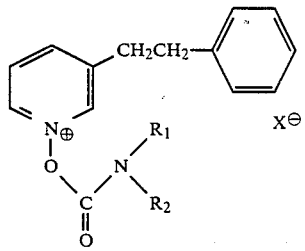

in which:
$R_1$ and $R_2$ are $C_{1-4}$ alkyl or, taken together with the nitrogen atom to which they are attached, prolidinyl or piperidinyl; and
X is chloro, bromo or iodo.

2. A compound of claim 1 in which $R_1$ and $R_2$ are methyl or ethyl.
3. A compound of claim 1 in which X is chloro.
4. A compound of claim 2 in which X is chloro.
5. A compound of claim 1 in which $R_1$ and $R_2$ are methyl and X is chloro.

* * * * *